United States Patent [19]

Jewart, Ronald D.

[11] Patent Number: 4,973,322
[45] Date of Patent: Nov. 27, 1990

[54] EYEDROPPER BOTTLE ATTACHMENT

[76] Inventor: Jewart, Ronald D., 2530 Twin Oaks Ct., Apt.8, Decatur, Ill. 62526

[21] Appl. No.: 379,102

[22] Filed: Jul. 13, 1989

[51] Int. Cl.$^5$ .............................................. A61M 35/00
[52] U.S. Cl. ..................................... 604/300; 604/302
[58] Field of Search ............... 604/294, 295, 298, 300, 604/301, 302, 214

[56] References Cited

U.S. PATENT DOCUMENTS

| | | |
|---|---|---|
| 3,934,590 | 1/1976 | Campagna . |
| 4,085,750 | 4/1978 | Bosshold . |
| 4,543,096 | 9/1985 | Keene .................................. 604/300 |
| 4,605,398 | 8/1986 | Herrick ................................ 604/300 |

FOREIGN PATENT DOCUMENTS 594860 3/1934 Fed. Rep. of Germany ...... 604/302

Primary Examiner—Stephen C. Pellegrino
Assistant Examiner—C. Maglione

[57] ABSTRACT

An attachment for an eye dropper bottle that aids in keeping the person's eyelids open while the bottle is being squeezed to insert/apply eyedrops into the eye. The attachment comprises two pivotably connected arms having laterally-projecting ears adapted to have edge contact with the person's eyelids. End areas of the arms can be engaged with the side surface of the person's nose to hold the attachment in a steady position or the arms can rest on the persons temple area. The squeeze bottle is offset to one side of the eye so that the eye and nozzle area of the bottle are made visible to the other eye.

5 Claims, 1 Drawing Sheet

EYEDROPPER BOTTLE ATTACHMENT

BACKGROUND AND SUMMARY OF THE INVENTION

This invention relates to a device usable with a squeeze type eye dropper bottle to keep a person's eyelids open while the bottle is being squeezed to spray eye solution into the eye. Many people find it difficult to keep the eyelids open while putting eye drop solutions into the eye; I have invented an attachment for an eye dropper bottle that can be actuated to automatically keep the eyelids open (separated) while the solution is being dropped into the eye.

Prior to my invention at least one device has been suggested for the purpose of keeping a person's eyelid open during the process of injecting solution into the person's eye. U.S. Pat. No. 4,085,750 to B. Bosshold shows an attachment 16 for an eye dropper bottle 10. The attachment comprises two flexible arms 18 having pads 22 adapted to engage the person's eyelids. Bottle 10 includes a nozzle 12 oriented to spray solution into the space between pads 22. In use of the attachment, flexible arms 18 are squeezed together, after which the attachment is manipulated so that pads 22 are pressed against the person's eyelids. When the pressure on the flexible arms is released the arms spring apart as shown in FIG. 2; this action causes the eyelids to separate. With the eyelids separated (opened) bottle 10 is squeezed to drop one or two drops of solution into the eye.

My invention relates to an attachment that is somewhat similar to the attachment shown in the Bosshold patent. However, in my proposed device the eyelid-engagement members are formed as thin laterally-projecting ears rather than large area pads. In use of my device the elongated arms are oriented laterally to one side of the eye, such that the person is enabled to use his other eye to see the eye being treated. This arrangement is different than that proposed in the Bosshold patent arrangement; in the Bosshold arrangement the eye dropper bottle and attachment are positioned substantially directly in front of the eye being treated so that it is difficult for the person to use his other eye to see into a mirror to see the bottle nozzle or the liquid being injected into the eye.

Another possible difficulty with the Bosshold arrangement is the fact that pads 22 are the only components in contact with the person's eye or adjacent head area; the attachment is steadied against the person's head only by reason of the pressure existing between pads 22 and the eyelid surfaces. If the manual pressure is excessive, the person is apt to feel some pain in the eye being treated. If the manual pressure is insufficient, the attachment may tend to slip away from the eyelids or become unsteady, i.e., wobble or shift back and forth.

My proposed attachment is designed so that end surfaces on the attachment arms can be engaged with the side area of the person's nose to steady the attachment device, or the device can be rested on the outer (temporal) portion of the eye. The arms can be swung toward the person's eye, using the side area of the person's nose as a fulcrum point. Pressure on the person's eyelids can be readily controlled while the device is held in a steady position against the side area of the person's nose.

In preferred practice of my invention, the eye dropper bottle is adjustably positioned on the attachment device so that the distance between the bottle and the person's eye can be varied according to individual desires.

THE DRAWINGS

FIG. 1 shows in dashed lines a partial outline of a person's eye-nose area, looking down from an imaginary point above the person's head.

DESCRIPTION OF A PREFERRED EMBODIMENT OF THE INVENTION

The drawings show an attachment device 10 for a conventional squeeze type eye dropper bottle 12 having a discharge nozzle 14. Bottle 12 is normally formed of a flexible plastic material, such that material pressure on the bottle side surfaces will cause eye solution to be directed into the person's eye. Arrows 16 in FIG. 1 indicate the direction such manual pressure would take. Bottle 12 may have a length of approximately two and one-half inches, but could be nearly any size.

Figure 1:
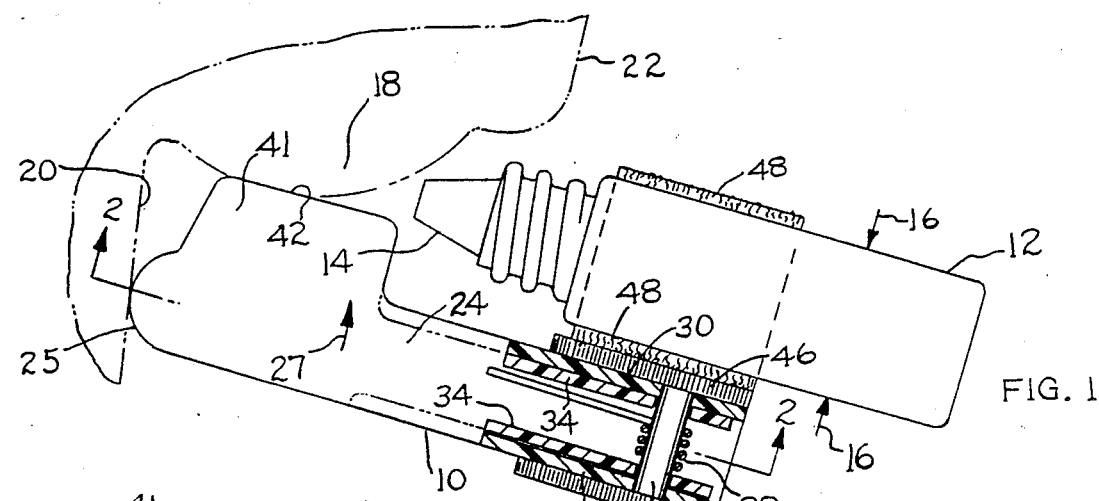
FIG. 1 is a sectional view taken on line 1—1 in FIG. 2, showing one embodiment of the invention.

FIG. 1 shows in dashed lines a person's eye 18, nose side surface 20, and temple surface 22. FIG. 1 is an overhead view looking down on the person's head. Attachment device 10 is shown with an end surface 25 thereof engaged against the person's nose side surface 20 to steady the attachment on the head. Bottle 12 is shown with nozzle 14 near, but out of contact with, eye 18 for discharging liquid solution onto the eye surface.

Figure 2:
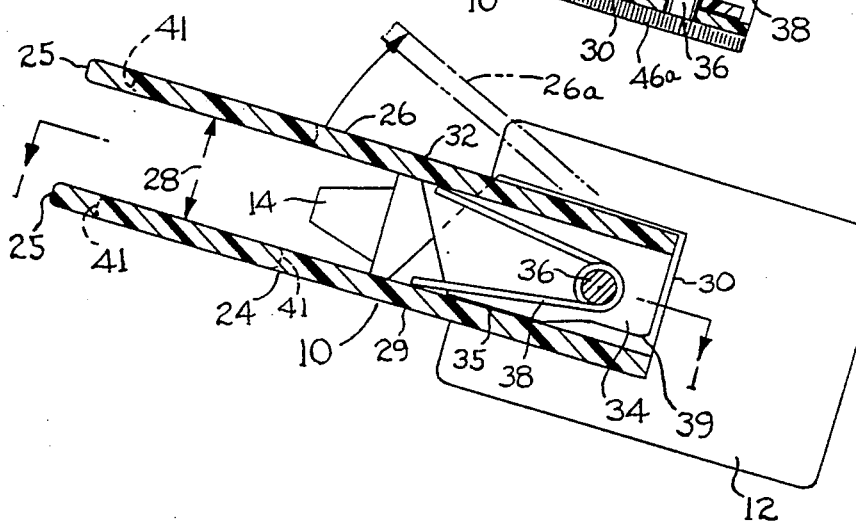
FIG. 2 is a sectional view taken on line 2—2 in FIG. 1.

Attachment device 10 comprises two elongated arms 24 and 26 spaced a slight distance apart, as indicated by numeral 28 in FIG. 2. Arm 24 comprises a flat main section 29 having two spaced parallel right angle flanges 30 at its right end forming a channel section. Arm 26 comprises a flat main section 32 having two spaced parallel right angle flanges 34 at its right end forming a second channel section. A pivot pin 36 extends transversely through flanges 30 and 34 so that arms 24 and 26 can swing around the pin axis. A wire spring 38 is coiled around pin 36 to urge arms 24 and 26 apart.

FIG. 2 illustrates arms 24 and 26 as being moved toward one another by manual pressure on flat sections 29 and 32. Edge surfaces 35 on flanges 34 engage the inner surface of arm 24 to limit motion of the arms toward each other. When manual pressure on arm sections 29 and 32 is lessened or removed spring 38 spreads the two arms apart; arm 26 swings away from arm 24 to approximately the dashed line position 26a in FIG. 2. Corner areas 39 on flanges 34 strike the inner face of arm 24 to limit the swinging motion of arm 26.

The left end section of each arm 24 or 26 is formed with a laterally projecting ear 41 having a relatively narrow edge surface 42. FIG. 1 shows the outline of the ear formed on arm 24. The ear formed on arm 26 is similarly configured. Edge surface 42 may have a thin rubber strip thereon to achieve a cushioned engagement between the edge surface and the person's eyelid; also, a silicon adhesive strip may be applied to edge surface 42 to assist in retaining the attachment device in engagement with the eyelid.

In use, the attachment device is positioned so that ear 41 on arm 24 engages the lower eyelid, and ear 41 on arm 26 engages the upper eyelid (with the two arms close together as shown in FIG. 2). Release of manual pressure on arms 24 and 26 enables arm 26 to swing to the dotted line position 26a, thereby forcing the upper eyelid open. Bottle 12 is then squeezed to spray one or more drops of liquid into the eye.

Bottle 12 may be adjustably attached (positioned) on attachment device 10 by means of adhesive patches affixed to the bottle and to a flange 30 on arm 24. As shown in FIG. 1, an adhesive patch 46 is affixed to flange 30 an adhesive sleeve 48 is attached to bottle 12.

Adhesive members 46 and 48 are preferably formed of miniature hook and loop materials sold under the trade name VELCRO. Such materials form multiple miniature interlocking connections when they are forced together; however the materials can be pried apart to break the connections. It thus became possible to relocate bottle 12 toward or away from the person's eye. Also the bottle direction can be changed slightly, if desired, to alter the direction of liquid movement into the person's eye.

Each arm 24 and 26 has a rounded end surface 25 adapted to engage the person's nose, such that attachment device 10 can be held in a steady position prior to bringing ears 41 into contact with eye 18 for discharging liquid solution onto the eye surface.

With end surface 25 engaged against the side area of the person's nose, the attachment device 10 can be rolled (swung) toward (or away from) the person's eye, as indicated generally by numeral 27 in FIG. 1. The pressure of ear edge surface 42 on the eyelids can thus be readily controlled.

The drawings show the attachment as used on the person's left eye. To use the attachment device on the person's right eye the bottle 12 is simply flipped over. A second patch 46a is affixed to the other flange, for flexibility of use.

A principle advantage of my proposed device is the fact that the eye dropper bottle is positioned laterally to one side of the eye being treated (rather than directly in front of the eye). The person is able to use his other eye to see the bottle discharge nozzle 14 and its orientation relative to the eye being treated.

Another advantage of my proposed device is the fact that it can be held steady against the person's nose, while the pressure on the eyelids is controlled or varied according to user preference.

The drawings show one form that the invention can take. Other forms are possible.

I claim:

1. An attachment for a squeeze type eye dropper bottle, comprising;
   a first elongated flat arm (24) having an end edge (25) adapted to engage the bridge area of a person's nose, and a laterally projecting ear (42) adapted to have edge engagement with a person's lower eyelid; a second elongated flat arm (26) having an end edge adapted to engage the bridge area of a person's nose, and a laterally projecting ear adapted to have edge engagement with a person's upper eyelid;
   means (36) pivotably connecting the two flat arms for relative swinging movement around a pivot axis located between the two arms and parallel to their flat planes;
   each projecting ear extending within the flat plane of the associated arm for edge engagement with a person's eyelid when the arms are extended laterally away from the person's nose and across the eye;
   said pivot means (36) being located between the two flat arms at a point remote from said projecting ears, whereby said ears can move appreciable distances toward or away from each other during relative swinging movements of the two arms;
   spring means (36) located between the two arms for biasing said arms away from each other in the absence of a manual squeezing force on the arms;
   and means (46, 48) for attaching an eyedropper bottle to one of said arms so that the spray axis of the bottle is normal to the aforementioned pivot axis and across the path taken by the projecting ears during relative swinging movement of the two elongated arms.

2. The attachment of claim 1, wherein said attachment means takes the form of adhesive patches carried by the bottle and said one arm.

3. The attachment of claim 1, wherein said end edge of each elongated flat arm has a curved profile, whereby the arms can be swung toward or away from the person's eye, using the side area of the person's nose as a fulcrum.

4. The attachment of claim 1, and further comprising two spaced parallel flanges extending right angularly from each elongated flat arm at locations remote from the associated ears; said pivot means comprising a pivot pin extending between said flanges, with the pin axis extending normal to the flange planes.

5. The attachment of claim 4, wherein said attachment means takes the form of adhesive patches carried by the bottle and one of the flanges.

* * * * *